(12) United States Patent  
Heath et al.

(10) Patent No.: US 9,187,503 B2  
(45) Date of Patent: Nov. 17, 2015

(54) OLEFINICALLY UNSATURATED PHOSPHONATE COMPOUNDS, POLYMERS MADE THEREFROM AND THEIR USE

(75) Inventors: Steve Heath, Aberdeen (GB); Gordon Moir, Aberdeenshire (GB); Marc Archibald, Aberdeenshire (GB); John Goulding, East Yorkshire (GB)

(73) Assignee: Clariant Finance (BVI) Limited, Tortola (VG)

( * ) Notice: Subject to any disclaimer, the term of this patent is extended or adjusted under 35 U.S.C. 154(b) by 1244 days.

(21) Appl. No.: 13/125,074

(22) PCT Filed: Oct. 6, 2009

(86) PCT No.: PCT/EP2009/007146  
§ 371 (c)(1),  
(2), (4) Date: Apr. 20, 2011

(87) PCT Pub. No.: WO2010/046026  
PCT Pub. Date: Apr. 29, 2010

(65) Prior Publication Data  
US 2011/0195876 A1 Aug. 11, 2011

(30) Foreign Application Priority Data  
Oct. 22, 2008 (EP) ................................. 08018433

(51) Int. Cl.  
*C09K 8/52* (2006.01)  
*C07F 9/38* (2006.01)  
*C02F 5/14* (2006.01)  
*C09K 8/528* (2006.01)  
*C09K 8/54* (2006.01)

(52) U.S. Cl.  
CPC ............... *C07F 9/3808* (2013.01); *C02F 5/14* (2013.01); *C09K 8/528* (2013.01); *C09K 8/54* (2013.01)

(58) Field of Classification Search  
None  
See application file for complete search history.

(56) References Cited

U.S. PATENT DOCUMENTS 2,867,286 A 2/1975 Quilan  
4,851,490 A 7/1989 Chen et al.  
5,855,622 A * 1/1999 Takeuchi .................. 8/111

OTHER PUBLICATIONS

Adusei et al., "Polymerization Behavior of an Organophosphorous Monomer for use in Dental Restorative Materials", J. of Applied Polymer Science, vol. 88, pp. 563-569 (2003).*  
International Search Report for PCT/EP2009/007146, mail dated Jan. 12, 2010.

* cited by examiner

Primary Examiner — John J Figueroa  
(74) Attorney, Agent, or Firm — Tod A. Waldrop

(57) ABSTRACT

This invention relates to compounds of formulae (1a) and (1b)

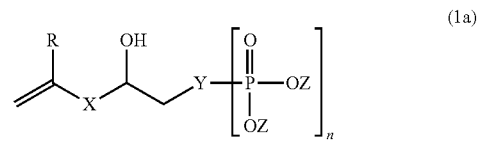

(1a)

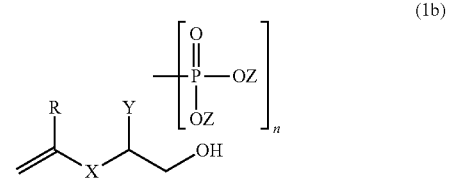

(1b)

wherein  
R means H or $C_1$- to $C_6$-alkyl,  
X is a structural unit selected from the formulae

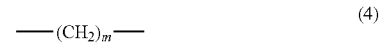

(4)

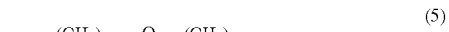

(5)

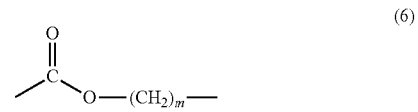

(6)

wherein m and k mean independently from each other a number from 1 to 12 for (4) and (5) and from 1 to 11 for (6),  
Y is a structural unit selected from the formulae

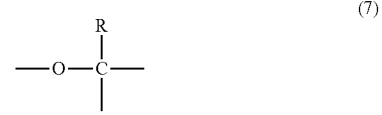

(7)

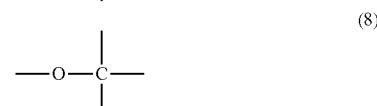

(8)

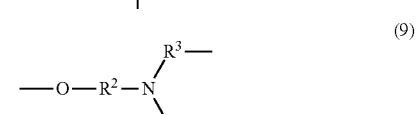

(9)

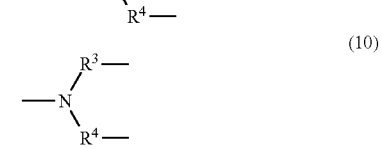

(10)

-continued

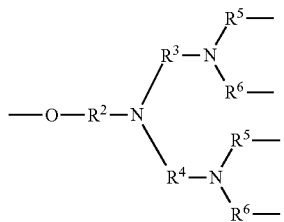
(11)

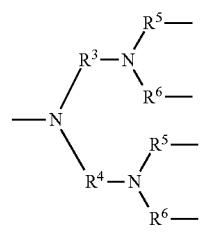
(12)

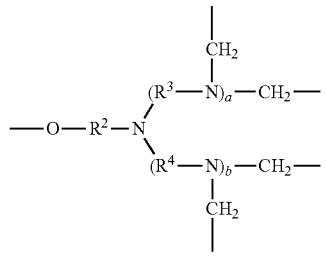
(13)

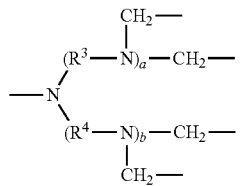
(14)

wherein a, b independently from each other are integers from 1 to 10

R means hydrogen or $C_1$- to $C_6$-alkyl $R^2$ means an alkylene or alkylidene group having 1 to 6 carbon atoms or an arylene or alkylarylene group having from 6 to 20 carbon atoms $R^3$, $R^4$, $R^5$, $R^6$ independently from each other mean an alkylene or alkylidene group having 1 to 6 carbon atoms or an arylene or alkylarylene group having from 6 to 20 carbon atoms, Z means a cation, and n means an integer being two or higher.

13 Claims, No Drawings

OLEFINICALLY UNSATURATED PHOSPHONATE COMPOUNDS, POLYMERS MADE THEREFROM AND THEIR USE

The present invention relates to novel phosphonate monomers, made by the reaction of ethylenically unsaturated substituted oxiranes with amine- or hydroxy-functional phosphonic acids or their precursors. These monomers may be polymerised or copolymerised with other ethylenically unsaturated species to yield phosphonate-functional polymers or oligomers. These polymers or oligomers are of particular use as oilfield scale inhibitors.

Water from natural sources often contains dissolved minerals, with an appreciable presence of ions such as $Ca^{2+}$, $Mg^{2+}$ and, in the case of oilfield formation water, $Ba^{2+}$, $Sr^{2+}$ and $Ra^{2+}$. Under conditions of temperature or pH change, loss of carbon dioxide from solution or admixture with other water containing differing mineral content, relatively insoluble species such as carbonates and sulphates may deposit from solution as scale. In offshore oilfields such deposition may be particularly acute when sulphate-containing seawater, pumped underground to aid oil recovery, comes into contact with the formation water.

Deposited scale impedes oil recovery and may even become severe enough to block an oilwell. It is therefore a common procedure to treat oilwells with a scale inhibitor to minimise or prevent scale deposition. These scale inhibitors are commonly oligomeric species, made by the free-radical interpolymerisation of monomers such as (meth)acrylic acid, maleic acid and sulphonated species such as 2-acrylamido-2-methylpropanesulphonic acid (AMPS®), allyl and vinyl sulphonic acid.

In use, a relatively concentrated solution of the scale inhibitor is pumped down the oilwell and flushed out into the formation. From here it leaches back in the produced water, protecting the well and pipework from scaling.

A careful balance of properties must be achieved. The scale inhibitor must not only control scale, but must also on the one hand have sufficient solubility in the waters at the temperatures it will meet to enable placement in the formation without itself prematurely precipitating from solution, whilst on the other hand it must adsorb strongly enough on the formation rock to give a suitable slow leach rate. If the scale inhibitor does not adsorb strongly enough it will all leach back very quickly and the well will require re-treatment after a short time.

It is also important that the concentration of scale inhibitor in the produced water can be monitored so that the progress of the leaching can be followed and the well re-treated before the scale inhibitor is depleted. Few of the oligomeric scale inhibitors referred to above lend themselves to ready quantitative analysis in produced water at the part-per-million levels involved.

Phosphorus-containing functional groups have been incorporated into scale inhibiting oligomers either by the use of hypophosphorous acid or its derivatives as telomerising agents (e.g. U.S. Pat. No. 4,046,707 and U.S. Pat. No. 6,071,434), or by the introduction of phosphorus-containing monomers such as vinyl phosphonic acid or vinylidene diphosphonic acid (e.g. EP-A-0 643 081). Such phosphorus functionality both aids the adsorption of the scale inhibitor onto the formation rock and also provides a useful analytical tag, whereby the scale inhibitor concentration can be calculated from an elemental phosphorus analysis. However, it is difficult to incorporate other than very low levels of phosphorus functionality via the telomerising agent route without reducing molecular weight to a performance-impairing level and the adsorption improvement is limited. The above phosphorus-containing monomers are difficult and expensive to make and polymerise, which again limits their level of use and performance improvement.

U.S. Pat. No. 3,799,893 discloses methylene phosphonates of glycidyl reacted polyalkylene polyamines, said methylene phosphonates of glycidyl reacted polyalkylene polyamines having nitrogen-bonded methylene phosphonate units and nitrogen-bonded glycidyl reacted units, said methylene phosphonates being of the formula

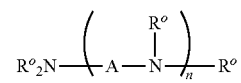

where
n is 1-100,
A is $-(OX_2)_m-$ where
m is 2 -10 and
X is hydrogen or alkyl, with the proviso that A is the same or different when n is 2, or more, and
$R^o$ is a methylene phosphonate unit, glycidyl reacted unit or hydrogen.

U.S. Pat. No. 4,851,490 discloses water soluble polymers containing an hydroxyl alkyl aminoalkylene phosphonate functionality which have utility as deposit control agents effective in a number of water systems such as cooling, boilers conversion coating, paper and pulp processing and gas scrubbing. The polymers are formed from the polymerization of ethylenically unsaturated compounds with a compound having the structure:

Adusei et al., J. of Applied Polymer Science, Vol. 88, 2003, pp. 565-569 discloses compounds of the formula

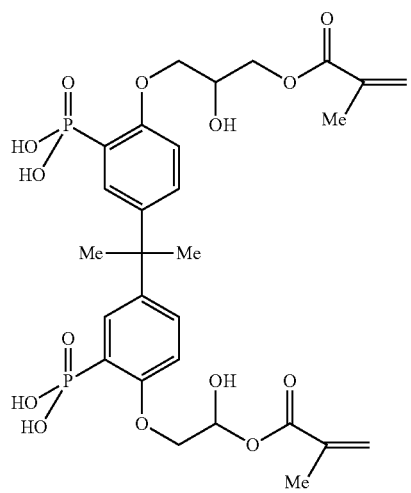 [SMILES: C=C(C)C(=O)OCC(O)COc1ccc(C(C)(C)c2ccc(OCC(O)OC(=O)C(=C)C)c(P(=O)(O)O)c2)cc1P(=O)(O)O]

its polymers and the polymers' use as dental restorative material.

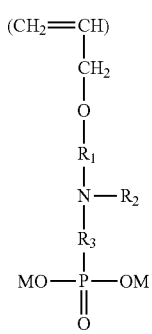

in which
R₁ is an hydroxyl substituted or nonsubstituted lower alkylene group,
R₂ is H or lower alkyl group,
R₃ is a lower alkylene group and
M is H or water soluble cation.

We have now discovered that ethylenically unsaturated oxiranes will readily react with hydroxy-functional phosphonates to make polymerisable phosphonate monomers. These will copolymerise with other monomers to give particularly useful oilfield scale inhibitors. This benefit stems partly from the possibility of incorporating higher levels of phosphorus functionality (in fact the phosphonate monomer can be the major monomeric component) into the oligomer and partly from the surprisingly favourable adsorption/desorption characteristics which it can impart. We postulate that the latter effect may be associated with the extensive complexing functionality afforded not only by the phosphonate moiety, but also by adjacent ether and hydroxyl groups. The relatively high level of phosphorus incorporation which is possible using these novel monomers also makes the analysis of the produced water for scale inhibitor content straightforward and accurate.

This invention relates to compounds of formulae (1a) and (1b):

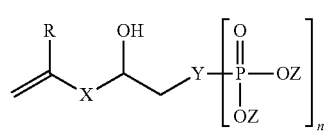

(1a)

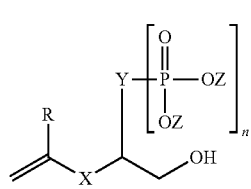

(1b)

wherein
R means H or $C_1$- to $C_6$-alkyl,
X is a structural unit selected from the formulae

—(CH₂)ₘ— (4)

—(CH₂)ₘ—O—(CH₂)ₖ— (5)

-continued

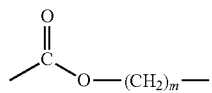

(6)

wherein m and k mean independently from each other a number from 1 to 12 for (4) and (5) and from 1 to 11 for (6),
Y is a structural unit selected from the formulae

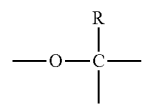

(7)

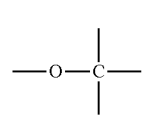

(8)

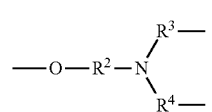

(9)

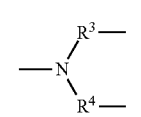

(10)

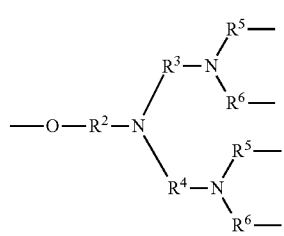

(11)

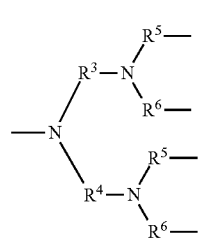

(12)

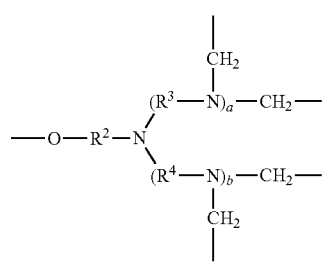

(13)

-continued

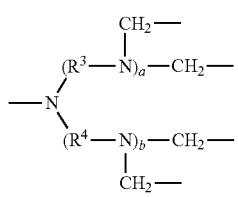
(14)

wherein a, b independently from each other are integers from 1 to 10

R means hydrogen or $C_1$- to $C_6$-alkyl $R^2$ means an alkylene or alkylidene group having 1 to 6 carbon atoms or an arylene or alkylaryfene group having from 6 to 20 carbon atoms $R^3$, $R^4$, $R^5$, $R^6$ independently from each other mean an alkylene or alkylidene group having 1 to 6 carbon atoms or an arylene or alkylarylene group having from 6 to 20 carbon atoms, Z means a cation, and n means an integer being two or higher.

This invention further relates to a process of manufacture of the compounds of formulae (1a) and (1b), the process comprising the step of reacting a compound of formula (2)

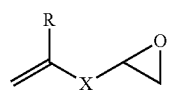
(2)

with a compound of formula (3)

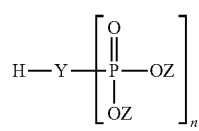
(3)

wherein R, X, Y, Z and n have the meaning as specified above.

This invention further relates to a process of manufacture of the compounds of formulae (1a) or (1b), the process comprising the steps of reacting a compound of formula (2)

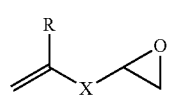
(2)

with an amidoalcohol or amidophenol, subsequently hydrolyzing the reaction product to yield an amine, and reacting said amine with formaldehyde and phosphorous acid to result in a compound of formulae (1a) or (1b).

This invention further relates to a process of manufacture of the compounds of formulae (1a) or (1b), the process comprising the steps of reacting a compound of formula (2)

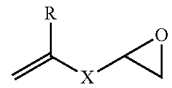
(2)

with ammonia or an amine, and reaction of the so obtained product with phosphorous acid and formaldehyde, to result in a compound of formulae (1a) or (1b).

This invention further relates to polymers and oligomers, obtainable by free radical homo- or copolymerization of the compounds of formulae (1a) and/or (1b).

This invention further relates to oligomers and polymers, comprising 2 wt.-% to 100 wt.-% of structural units of the formulae (1c) and/or (1d)

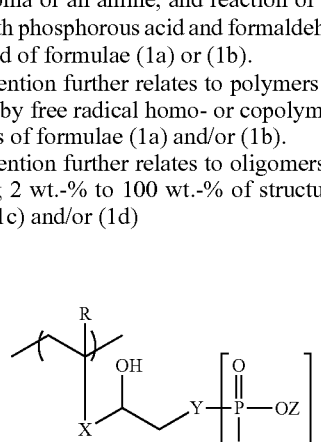
(1c)

(1d)

the polymers having a molecular weight of from 800 to 30,000 g/mol, wherein R, X, Y, Z and n have the meaning as specified above.

This invention further relates to a process of inhibiting scale deposition from an aqueous system, the process comprising the step of adding an oligomer or polymer as described above to the aqueous system.

This invention further relates to the use of oligomers or polymers as described above as scale inhibitors in aqueous systems.

n is preferably an integer from 2 to 80, particularly from 3 to 40, for example 2, 3, 4, 5, 6, 7, 8, 9 or 10.

In a preferred embodiment of the invention X means groups corresponding to the formulae

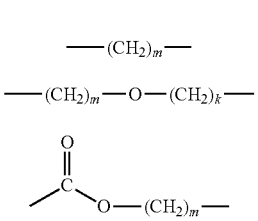
(4)
—$(CH_2)_m$—

(5)
—$(CH_2)_m$—O—$(CH_2)_k$—

(6)

wherein m and k being independently from each other a number from 2 to 6. As an example, X may be —$(CH_2)$—O—$(CH_2)$—.

In the formulae (7) to (14), Y is shown in the same direction as represented in formulae (1a) and/or (1b), i.e. the unsaturated residue of the molecule is bonded to Y via the valency shown on the left and the phosphonic acid or salt groups are bonded to the valencies on the right.

Z is any suitable cation. Preferably, Z is selected from hydrogen, alkali metal, alkaline earth metal, ammonium or organic base cations.

A particularly preferred compound of formula (1a) corresponds to the formula (15)

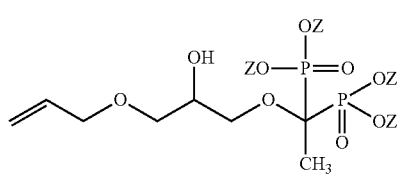
(15)

Another particularly preferred compound of formula (1a) corresponds to the formula (16)

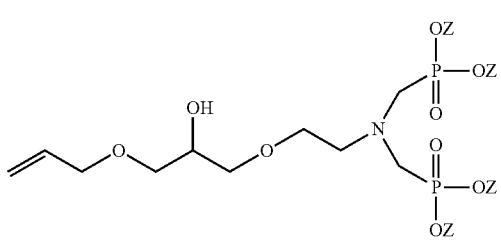
(16)

Another particularly preferred compound of formula 1(a) corresponds to the formula (17)

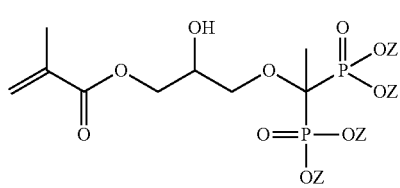
(17)

Another particularly preferred compound of formula 1(a) corresponds to the formula (18)

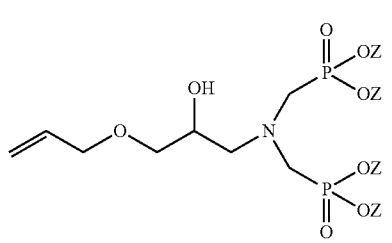
(18)

Another particularly preferred compound of formula 1(a) corresponds to the formula (19)

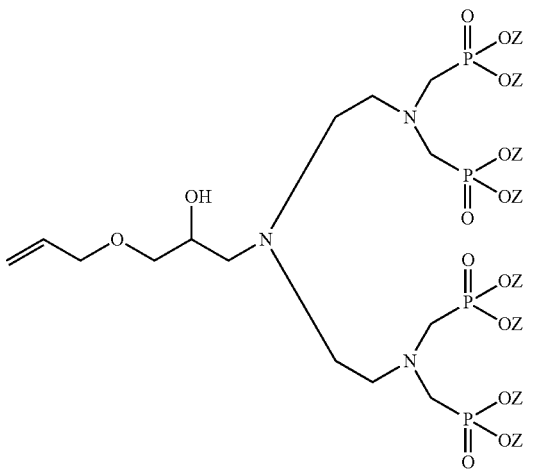
(19)

The phosphonates of the invention and the phosphonic acids used as starting material to make them may exist either as the free acid or as their salts. It should be understood that references made here to the acid also pertain to the salts and vice versa where the context makes this possible.

Polymers and oligomers made from these novel phosphonate monomers, and optionally other comonomers, are particularly useful as oilfield scale inhibitors.

The phosphonate monomers of the invention may be made by the reaction of ethylenically unsaturated oxiranes (e.g. allylglycidyl ether or glycidyl methacrylate) with hydroxy-functional phosphonic acids (e.g. hydroxyethylidenediphosphonic acid or 2-hydroxyethyliminobismethyl-enephosphonic acid [monoethanolamine diphosphonate]).

The reaction is preferably carried out in an aqueous medium under mildly alkaline conditions, though the use of organic solvents and/or acidic catalysis is possible. Although the ethylenically unsaturated oxiranes may be relatively sparingly soluble in water, given adequate agitation of the heterogeneous mixture they react readily. The product phosphonate monomer may tend to crystallise out during the process if the concentration of the reaction mixture is high. In order to avoid this and to produce a stable monomer solution it is preferred to operate below 50% solids, more typically at 30-40% solids. The preferred process temperature is about 75-95° C., at which reaction is generally complete in a few hours. Higher reaction temperature under aqueous conditions may lead to reduced yield of the phosphonate monomer, owing to did formation by reaction of the oxirane with water.

The following examples illustrate how the compounds of formula (1a) and (1b) can be manufactured.

allyl glycidyl ether

+ hydroxy ethylidene diphosphonic acid

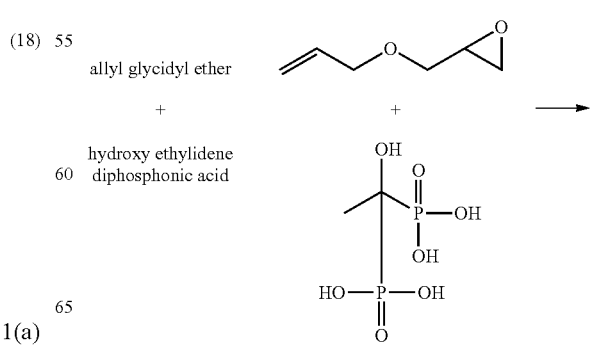

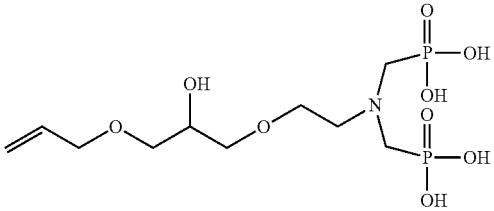

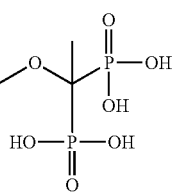

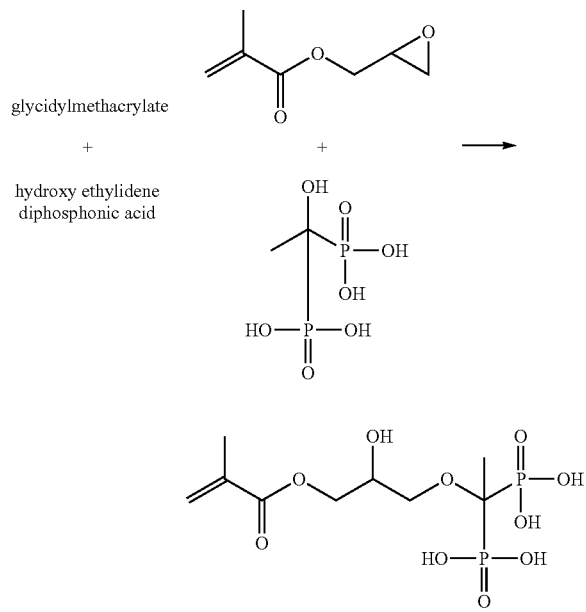

Any such reaction will result in a mixture of compounds of formulae (1a) and (1b).

Another way of making the phosphonate monomers of the invention is to react an amidoalcohol or amidophenol (e.g. N-acetylethanolamine) with an ethylenically unsaturated oxirane (e.g. allyl glycidyl ether) to yield an intermediate, which on hydrolysis gives an amine which can be reacted with formaldehyde and phosphorous acid (Mannich reaction) to give phosphonate monomers. Typically the first step of this synthesis is done under anhydrous conditions using a basic catalyst, though again an acid catalyst is feasible. Reaction temperature is typically in the range of 100-150 °C. The hydrolysis and Mannich reaction is usually done under aqueous acidic conditions, typically at 80-110 °C. for several hours. A reaction scheme could look as follows:

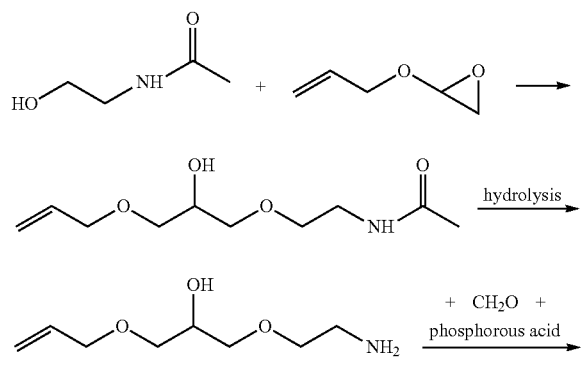

A further way of making the phosphonate monomers of the invention is to react ammonia or an amine with an ethylenically unsaturated oxirane to make an unsaturated aminofunctional intermediate which can be reacted with formaldehyde and phosphorous acid (Mannich reaction) to give phosphonate monomers. With this procedure steps may be taken to minimise the formation of polyunsaturated species (e.g. using a large excess of ammonia or amine). The oxirane reaction may be done with or without a solvent, but generally an aqueous medium is preferred, with the reaction temperature between 40 and 100° C. for a period of a few hours. The Mannich reaction is done as above.

The phosphonate monomers of the invention may be (co) polymerised by well-known free-radical processes. Typically this can be done in aqueous solution, with water-soluble polymerisation initiators, catalysts, chain transfer agents and comonomers. However, polymerisation in an organic solvent or use of emulsion or suspension type polymerisation processes and the use of water-insoluble reactants is also possible.

The polymers may be homopolymers of the compounds of formulae (1a) or (1b), or copolymers comprising 2 to less than 100 wt.-% of the structural elements of formulae (1c) or (1d) and up to 98 wt.-% of other monomers. As monomers besides the compounds of formulae (1a) or (1b) olefinically unsaturated compounds are suitable. Preferred olefinically unsaturated compounds are selected from mono- and dicarboxylic acids and their derivatives, such as salts, esters and amides. Other preferred olefinically unsaturated compounds are sulphonic acids and their derivatives, such as salts.

Examples of preferred olefinically unsaturated compounds to form copolymers with the compounds of formulae (1a) or (1b) are acrylic acid and its esters and salts, methacrylic acid and its esters and salts, maleic acid and its esters and salts, fumaric acid and its esters and salts, crotonic acid and its esters and salts, itaconic acid and its esters and salts, mesaconic acid and its esters and salts, citraconic acid and its esters and salts, angelic acid, vinyl acetate, vinyl chloride, vinyl pyridine, vinyl pyrrolidone, acrylamide and its derivatives, 2-acrylamido-2-methylpropane sulphonic acid and its salts, styrene-4-sulphonic acid and its salts, allyl sulphonic acid and its salts, methallylsulphonic acid and its salts, vinyl sulphonic acid and its salts, vinyl phosphonic acid and its salts, dialkylaminoacrylates and methacrylates and their quaternary derivatives, diallyldimethylammonium chloride and 3-allyloxy-2-hydroxypropyltrimethylammonium chloride.

Examples of polymerisation initiators which may be used include alkali metal and ammonium persulphates, hydrogen peroxide, organic peroxides, azo compounds and redox couples such as persulphate/bisulphite, peroxide/hypophosphite, hydroperoxide/formaldehyde sulphoxylate.

Examples of catalysts which may be used include iron and copper salts. Examples of chain-transfer reagents which may be used include thiols such as mercaptoacetic acid and mercaptopropionic acid, secondary alcohols such as isopropanol and hypophosphorous acid and its salts.

For the oilfield scale inhibitor application the molecular weight of the polymers or oligomers preferably should be in the range from about 1000-20000 g/mol, more typically from 1500-5000 g/mol. This may be achieved by the well-known means of initiator and chain transfer agent level adjustment.

Apart from a use as scale inhibitor, the polymers of the invention are suitable as corrosion inhibitors, scale dissolvers, adhesion promoters, detergent builders, deflocculants and dispersants.

The polymers of the invention are used in concentrations suitable to fulfill their purpose. In general, the concentration of use is between 1 and 10,000 ppm, more particularly between 3 and 1000 ppm.

For the oilfield scale inhibitor application the polymers or oligomers are generally based on compositions using from 2 wt.-% to 100 wt.-% of the phosphonate monomer in the total monomer. More typically 3 wt.-% to 60 wt.-% of the phosphonate monomer is preferred.

Polymerisation may be conducted by batch, semi-continuous or continuous processes.

The following examples further illustrate the invention:

EXAMPLE 1

Monomer 36 g of a 60% aqueous solution of hydroxyethylidenediphosphonic acid and 40 g of water was placed in a reaction vessel equipped with stirring, reflux condenser and heating and cooling. With stirring and cooling 33.6 g of 50% sodium hydroxide was added slowly. 11.4 g of allylglycidyl ether was then added and the mixture heated to 80° C. and kept at this temperature for 2 hours, then heated to 95° C. and kept at this temperature for 1 hour. The reaction mixture was then cooled and could be used, without further purification, as a monomer solution.

If the cooled reaction mixture was extracted with ether (3×) and the combined ether extracts dried and evaporated, a negligible amount of allyiglyceryl ether was isolated. If the aqueous solution remaining after ether extraction was dried at 105° C. to constant weight, about 38 g or approximately 88% of the theoretical quantity of diphosphonate monomer was obtained as a white solid.

EXAMPLE 2

Monomer 72 g of a 60% aqueous solution of 1,1-hydroxyethylidenediphosphonic acid and 160 a of water was placed in a reaction vessel equipped with stirring, reflux condenser and heating and cooling. With stirring and cooling 60 g of 50% sodium hydroxide was added slowly. 0.015 g of p-methoxyphenol and 28.4 g of glycidyl methacrylate were then added and the mixture heated to 75° C. for 7 hours. A small amount of unreacted glycidyl methacrylate was separated off and the product either isolated as a white, crystalline solid (approx. 70% yield) or used as the unpurified aqueous solution to make polymers.

EXAMPLE 3

Monomer 51.5 g of N-acetylethanolamine and 0.275 g of sodium metal were placed in a reaction vessel equipped with stirring, reflux condenser and heating and cooling. The mixture was heated to 130° C. and when the sodium was fully dissolved 57 g of allyl glycidyl ether was added in small portions over 1 hour. The temperature was kept at 130-140° C. throughout the addition and for 1.5 hours after.

The reaction mixture was then cooled and 27.5 g of 37% hydrochloric acid was added, followed by 88.5 g of 97% phosphorous acid and 24.5 g of water. The mixture was then heated to 93° C. and 92.5 g of 34% formaldehyde solution was added over 30 mins., keeping the temperature at 90-95° C. When all the formaldehyde was added the temperature was raised to reflux (105-108° C.) for 10 hours.

After cooling 15.5 g of 50% sodium hydroxide was added. The resulting solution was used without purification to make copolymers.

EXAMPLE 4

Monomer 250 g of 0.880 ammonia and 57 g of allyl glycidyl ether were placed in a reaction vessel equipped with stirring, reflux condenser and heating and cooling. A slow reaction ensued, the temperature rising to a peak of 40° C. without the application of external heating. Heating was then applied and the mixture refluxed until ammonia was not detected in the exit gas (3 hours approx.).

The reaction mixture was then cooled and 27.5 g of 37% hydrochloric acid was added, followed by 88.5 g of 97% phosphorous acid and 24.5 g of water. The mixture was then heated to 93° C. and 92.5 g of 34% formaldehyde solution was added over 30 mins., keeping the temperature at 90-95° C. When all the formaldehyde was added the temperature was raised to reflux (105-108° C.) for 10 hours.

After cooling 15.5 g of 50% sodium hydroxide was added. The resulting solution was used without purification to make copolymers.

EXAMPLE 5

Monomer 25.75 g of diethylenetriamine and 62.5 g of water were placed in a reaction vessel equipped with stirring, reflux condenser and heating and cooling. With cooling, 49.25 g of 37% hydrochloric acid was added slowly. The temperature was reduced to 40° C. and then 28.5 g of allyl glycidyl ether was added. The mixture was heated to 65-70° C. for 1 hour, then raised to 95° C. for 1 hour.

The reaction mixture was then cooled and 88.5 g of 97% phosphorous acid and 30 g of water were added.

The mixture was then heated to 93° C. and 92.5 g of 34% formaldehyde solution was added over 30 mins., keeping the temperature at 90-95° C. When all the formaldehyde was added the temperature was raised to reflux (105-108° C.) for 10 hours.

After cooling 27.7 g of 50% sodium hydroxide was added. The resulting solution was used without purification to make copolymers.

EXAMPLE 6

Polymer 121 g of the-reaction mixture from Example 1 was copolymerised in aqueous solution with 130 g of sodium allylsulphonate and 98 g of maleic anhydride.

The resulting product was a clear, light brown solution at 51% non-volatiles, pH 2, Brookfield viscosity 62 cP.

The resulting product has been tested in a series of comparative tests against a number of industry standard scale inhibitors. This testing included static and dynamic inhibition tests in a sulphate scaling regime (represented by a 50:50 formation water (250 mg/l Barium): seawater (2960 mg/l Sulphate) brine mix), dynamic inhibition performance testing with a carbonate scaling regime (represented by, a self-scaling formation water (2800 mg/l Calcium, 500 mg/l Bicarbonate), a modified static test to evaluate the performance in a sulphide scaling regime and a static adsorption test to evaluate the retention characteristics offered by the polymer.

The polymer demonstrated excellent performance towards sulphate scale in both static and dynamic inhibition tests, offering a higher degree of inhibition efficiency and lower MIC's compared with the industry standards, see Tables 1 and 2. It is also clear that the inclusion of the phosphonate monomer has improved the sulphate inhibition performance under both static and dynamic conditions when compared to the non P containing polymers, see Tables 1 and 2. This is perceived to be due synergistic inhibition gained from the combination of the phosphonate and the maleic and sulphonate functional groups in the polymer. The polymer also demonstrated a reasonable degree of carbonate inhibition in dynamic testing, the results of which are presented in Table 3.

TABLE 1

Static inhibition testing of Example 6 under sulphate conditions over 24 hrs; values give Ba efficiency in %

| Inhibitor | Inhibitor Concentration/ppm | | |
|---|---|---|---|
| | 5 | 10 | 15 |
| DTPMP (comp) | 8 | 20 | 42 |
| PPCA (comp) | 14 | 17 | 18 |
| HEMPA (comp) | 12 | 13 | 15 |
| Maleic acid terpolymer (comp) | 8 | 8 | 9 |
| PVS copolymer (comp) | 8 | 52 | 65 |
| Example 6 | 48 | 82 | 100 |

TABLE 2

Dynamic inhibition testing of Example 6 under sulphate conditions

| Inhibitor | Minimum Inhibitor Concentration/ppm |
|---|---|
| DTPMP (comp) | 15 |
| PPCA (comp) | 20 |
| HEMPA (comp) | >30 |
| Maleic acid terpolymer (comp) | 30 |
| PVS copolymer (comp) | 30 |
| Example 6 | 15 |

TABLE 3

Dynamic inhibition testing of Example 6 under carbonate conditions

| Inhibitor | Minimum Inhibitor Concentration/ppm |
|---|---|
| Example 6 | 1 |

In static tests the polymer has also shown a degree of inhibition towards iron sulphide scales showing a higher tolerance to sulphide through addition of increasing concentrations of sulphide anion to an iron containing (10 ppm) brine mix, the results are presented in Table 4.

TABLE 4

Static sulphide tolerance testing under sulphide scaling conditions, 100 ppm inhibitor concentration; values indicate turbidity in ntu

| Inhibitor | added sulphide in ppm | | | | |
|---|---|---|---|---|---|
| | 10 | 15 | 20 | 25 | 30 |
| none | 250 | 300 | — | — | — |
| PPCA (comp) | 50 | 120 | 300 | 430 | 480 |
| HEMPA (comp) | 90 | 200 | 320 | 400 | 400 |
| PVS copolymer (comp) | 120 | 280 | 400 | 480 | 480 |
| Maleic acid terpolymer (comp) | 30 | 50 | 120 | 300 | 450 |
| Example 6 | 90 | 210 | 400 | 420 | 450 |
| Example 11 | 30 | 110 | 260 | 420 | 500 |

The resultant polymer has also shown an increase in adsorption onto sandstone core material in static adsorption tests compared with non-P-containing products, see Table 5. This result is to be expected as it is well documented that the inclusion of P-containing groups in polymers via a back bone or a side chain increases the retention of the polymer onto rock surfaces.

TABLE 5

Static adsorption of inhibitors on sandstone in mg/g

| Inhibitor | Inhibitor adsorpiton time, hrs | | | | | |
|---|---|---|---|---|---|---|
| | 0.5 | 1 | 2 | 4 | 6 | 24 |
| VS copolymer (comp) | 0 | 0 | 0.7 | 0.5 | 0.6 | 0 |
| DTPMP (comp) | 6 | 8 | 9 | 10 | 10.5 | 10.5 |
| PVS copolymer (comp) | 0 | 0.1 | 0.2 | 0.3 | 0.6 | — |
| Example 6 | 1.5 | 2.5 | 2.5 | 2.8 | 3.0 | 3.5 |
| Example 7 | 0 | 1 | 3.2 | 3.2 | 5 | 7 |
| Example 11 | 1.5 | 5.5 | 7 | 7 | 8.5 | 9.5 |

In the testing performed here the resultant polymer has demonstrated effective performance against sulphate, carbonate and sulphide scales and a high level of adsorption onto sandstone core.

EXAMPLE 7

Polymer

Preparation of a diphosphonate-functional oligomer with a higher diphosphonate content.

242 g of the reaction mixture from Example 1 was copolymerised in aqueous solution with 48 g of sodium allylsuiphonate and 49 g of maleic anhydride.

The resulting product was a clear, light brown solution at 42% non-volatiles, pH 3.0, Brookfield viscosity 14 cP.

The resulting product has been tested in a series of comparative tests against a number of industry standard scale inhibitors. This testing included static and dynamic inhibition tests in a sulphate scaling regime (represented by a 50:50 formation water (250 mg/l Barium): seawater (2960 mg/l Sulphate) brine mix). In both static and dynamic inhibition tests the polymer demonstrates effective performance against sulphate scales, the results are presented in Tables 6 and 7.

TABLE 6

Static inhibition testing of Example 7 under sulphate conditions
over 24 hrs; values indicate the Ba efficiency in %

| | Inhibitor Concentration/ppm | | |
|---|---|---|---|
| Inhibitor | 5 | 10 | 15 |
| DTPMP (comp) | 8 | 20 | 42 |
| PPCA (comp) | 14 | 17 | 18 |
| HEMPA (comp) | 12 | 13 | 15 |
| Maleic acid terpolymer (comp) | 8 | 8 | 9 |
| PVS copolymer (comp) | 8 | 52 | 65 |
| Example 7 | 32 | 50 | 72 |

TABLE 7

Dynamic inhibitor testing of example 7 under sulphate conditions

| Inhibitor | Minimum Inhibitor Concentration/ppm |
|---|---|
| DTPMP (comp) | 15 |
| PPCA (comp) | 20 |
| HEMPA (comp) | >30 |
| Maleic acid terpolymer (comp) | 30 |
| PVS copolymer (comp) | 30 |
| Example 7 | 20 |

The resultant polymer has also shown a high degree of adsorption onto sandstone core material in static adsorption tests, the results are presented in Table 5.

EXAMPLE 8

Polymer 316 g of the product from Example 2 was homopolymerised in aqueous solution.

The clear, slightly yellow product had a non-volatile content of 19%, pH 7.7 and Brookfield viscosity of 3 cP.

EXAMPLE 9

Polymer 75 g of the solution from Example 3 was copolymerised in aqueous solution with 143 g of acrylic acid.

The clear, pale brown product had a non-volatile content of 41%, pH 4.4 and Brookfield viscosity of 99 cP.

The resultant product has been evaluated in dynamic tests in a carbonate scaling regime (represented by self scaling formation water (2800mg/l Calcium, 500mg/l Bicarbonate)). The polymer demonstrates effective inhibition of carbonate scales with results presented in Table 8.

TABLE 8

Dynamic inhibition testing of Example
9 under carbonate conditions

| Inhibitor | Minimum Inhibitor Concentration/ppm |
|---|---|
| Example 9 | 4 |

EXAMPLE 10

Polymer 90 g of the solution from Example 4 was copolymerised in aqueous solution with 72 g of acrylic acid and 65 g of sodium vinyl sulphonate.

The clear, pale brown product had a non-volatile content of 41%, pH 3.3 and Brookfield viscosity of 21 cP.

The resulting product has been tested in dynamic inhibition tests in a sulphate scaling regime (represented by a 50:50 formation water (250 mg/l Barium): seawater (2960 mg/l Sulphate) brine mix). In the tests performed here the polymer demonstrates excellent inhibition of sulphate scales, the results are presented in Table 9.

TABLE 9

Dynamic inhibition testing of Example
10 under sulphate conditions

| Inhibitor | Minimum Inhibitor Concentration/ppm |
|---|---|
| DTPMP (comp) | 15 |
| PPCA (comp) | 20 |
| HEMPA (comp) | >30 |
| Maleic acid terpolymer (comp) | 30 |
| PVS copolymer (comp) | 30 |
| Example 10 | 20 |

EXAMPLE 11

Polymer 108 g of the solution prepared in Example 5 was copolymerised in aqueous solution with 77 g of sodium allylsulphonate and 65 g of maleic anhydride.

The resulting product was a clear, light brown solution at 53% solids, pH 1.3 and Brookfield viscosity 66 cP.

The resulting product has been tested in a series of comparative tests against a number of industry standard scale inhibitors. This testing included static and dynamic inhibition tests in a sulphate scaling regime (represented by a 50:50 formation water (250 mg/l Barium): seawater (2960 mg/l Sulphate) brine mix). In both static and dynamic inhibition tests the polymer demonstrates effective performance against sulphate scales, the results are presented in Tables 10 and 11.

TABLE 10

Static inhibition testing of Example 11 under sulphate conditions
over 24 hrs; values indicate the Ba efficiency in %

| | Inhibitor Concentration/ppm | | |
|---|---|---|---|
| Inhibitor | 5 | 10 | 15 |
| DTPMP (comp) | 8 | 20 | 42 |
| PPCA (comp) | 14 | 17 | 18 |
| HEMPA (comp) | 12 | 13 | 15 |
| Maleic acid terpolymer (comp) | 8 | 8 | 9 |
| PVS copolymer (comp) | 8 | 52 | 65 |
| Example 11 | 12 | 75 | 58 |

TABLE 11

Dynamic inhibition testing of Example
11 under sulphate conditions

| Inhibitor | Minimum Inhibitor Concentration/ppm |
|---|---|
| DTPMP (comp) | 15 |
| PPCA (comp) | 20 |
| HEMPA (comp) | >30 |
| Maleic acid terpolymer (comp) | 30 |

TABLE 11-continued

Dynamic inhibition testing of Example 11 under sulphate conditions

| Inhibitor | Minimum Inhibitor Concentration/ppm |
|---|---|
| PVS copolymer (comp) | 30 |
| Example 11 | 25 |

The resultant polymer has also shown a high degree of adsorption onto sandstone core material in static adsorption tests, the results are presented in Table 5.

The abbreviations have the following meanings
DTPMP Diethylenetriamine-penta-methylene phosphonic acid disodium salt
PPCA Polyphosphinocarboxylic acid
HEMPA Hydroxyethyiamino-di(methyiene phosphonic acid)
PVS Polyvinyl sulphonate

The invention claimed is:
1. A compound of formulae (1 a) and (1 b)

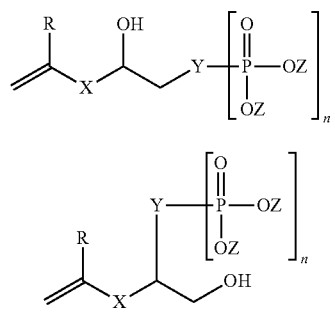

wherein
R is a H or $C_1$- to $C_6$-alkyl,
X is a structural unit selected from the group consisting of formulae

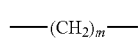  (4)

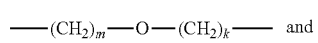  (5)

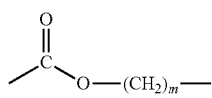  (6)

wherein m and k are independently from each other a number from 1 to 12 for (4) and (5) and from 1 to 11 for (6),
Y is a structural unit selected from the group consisting of formulae

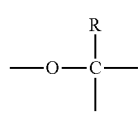  (7)

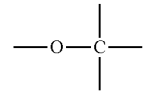  (8)

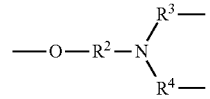  (9)

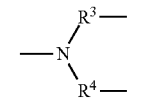  (10)

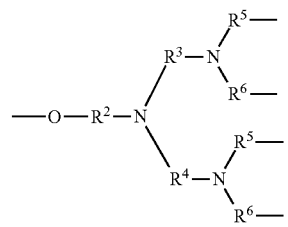  (11)

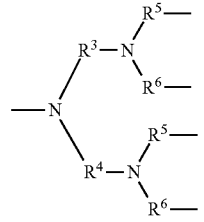  (12)

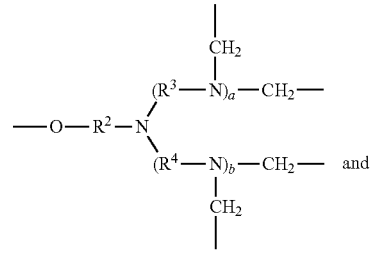  (13)

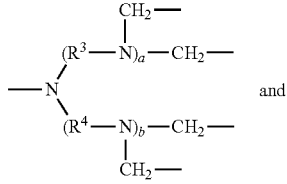  (14)

wherein
a, b independently from each other are integers from 1 to 10
R is a hydrogen or $C_1$- to $C_6$-alkyl
$R^2$ is an alkylene or alkylidene group having 1 to 6 carbon atoms or an arylene or alkylarylene group having from 6 to 20 carbon atoms
$R^3$, $R^4$, $R^5$, $R^6$ independently from each other are an alkylene or alkylidene group having 1 to 6 carbon atoms or an arylene or alkylarylene group having from 6 to 20 carbon atoms,
Z is a cation, and
n is an integer being two or higher.
2. A compound according to claim 1, wherein X is —($CH_2$)—O—($CH_2$)—.

3. A compound according to claim 1, wherein Z is selected from the group consisting of an alkali metal, alkaline earth metal, ammonium and organic base cations.

4. A compound according to claim 1, corresponding to one of the formulae (15) to (19)

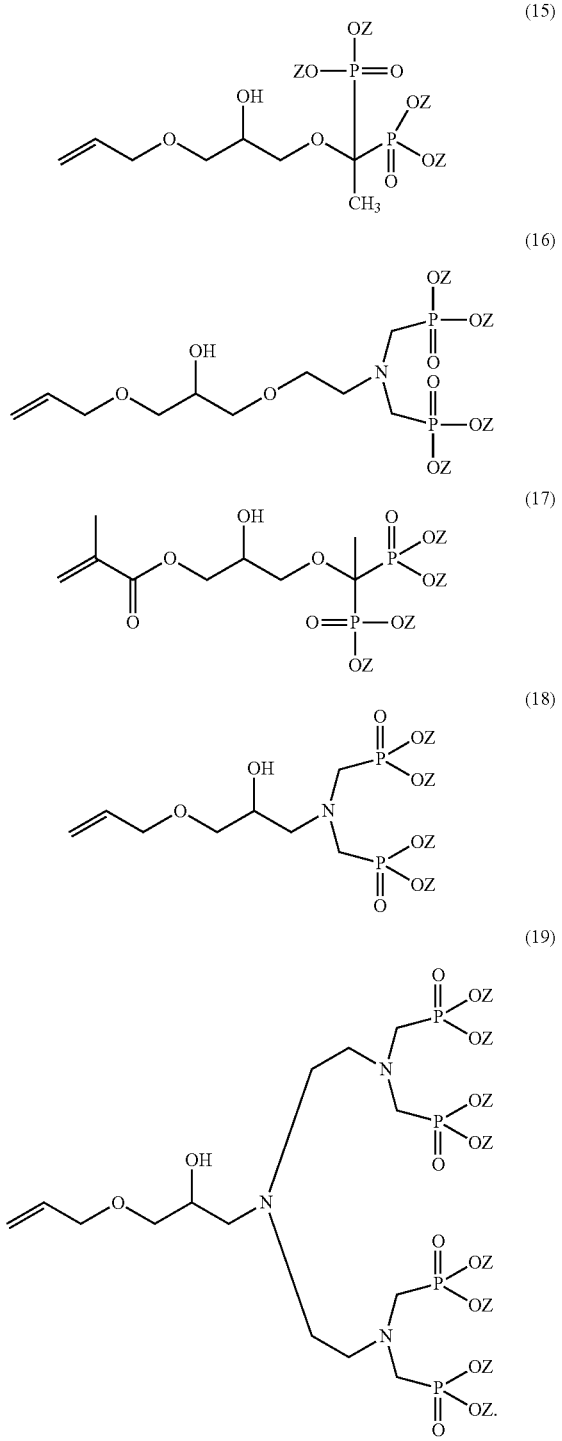

5. A polymer and oligomer, comprising 2 wt.-% to 100 wt.-% of repetitive structural units of the formulae (1c) and/or (1d)

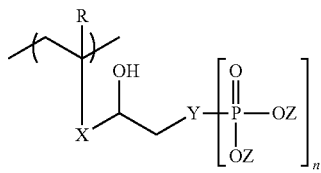

(1c)

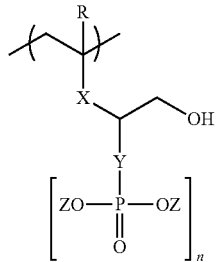

(1d)

the polymers having a molecular weight of from 800 to 30,000 g/mol, wherein R, X, Y, Z and n are defined as in claim 1.

6. A polymer and oligomer according to claim 5, where the monomers copolymerised with the repetitive structural units of the formulae (1c) and/or (1d)

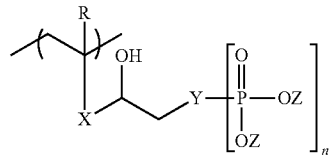

(1c)

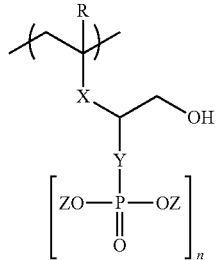

(1d)

wherein R, X, Y, Z and n are defined as in claim 5, are selected from the group consisting of acrylic acid and its esters and salts, methacrylic acid and its esters and salts, maleic acid and its esters and salts, fumaric acid and its esters and salts, crotonic acid and its esters and salts, itaconic acid and its esters and salts, mesaconic acid and its esters and salts, citraconic acid and its esters and salts, angelic acid, vinyl acetate, vinyl chloride, vinyl pyridine, vinyl pyrrolidone, acrylamide and its derivatives, 2-acrylamido-2-methylpropane sulphonic acid and its salts, styrene-4-sulphonic acid and its salts, allyl sulphonic acid and its salts, methallylsulphonic acid and its salts, vinyl sulphonic acid and its salts, vinyl phosphonic acid and its salts, dialkylaminoacrylates and methacrylates and their quaternary derivatives, diallyldimethylammonium chloride and 3-allyloxy-2-hydroxypropyltrimethylammonium chloride.

7. A polymer and oligomer according to claim 5, wherein the acid groups are fully or partially neutralised to form salts with one or more cations selected from the group consisting of sodium, potassium, calcium, magnesium, aluminum, zinc, ammonium, the cations derived from the amines mono, di or trimethylamine, mono, di or triethylamine, monoethanolamine, diethanolamine, and triethanolamine.

8. A process of manufacture of the compounds according to claim 1, wherein the process comprises the step of reacting a compound of formula 2

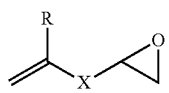 (2)

with a compound of formula 3

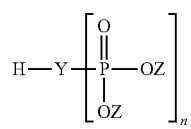 (3)

wherein
R is a H or $C_1$- to $C_6$-alkyl,
X is a structural unit selected from the group consisting of formulae

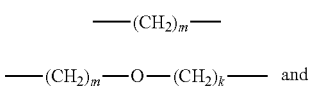 (4) (5)

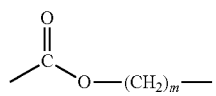 (6)

wherein m and k are independently from each other a number from 1 to 12 for (4) and (5) and from 1 to 11 for (6),
Y is a structural unit selected from the group consisting of formulae

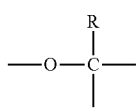 (7)

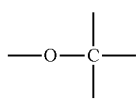 (8)

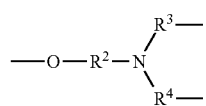 (9)

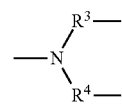 (10)

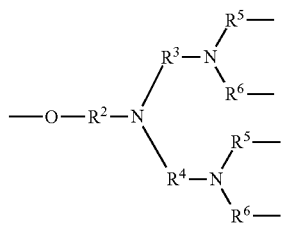 (11)

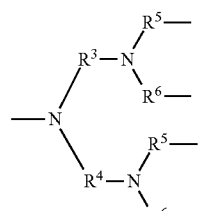 (12)

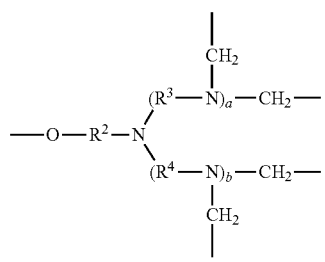 (13)

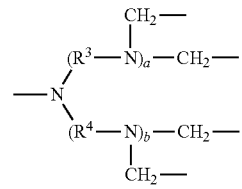 (14)

wherein
a, b independently from each other are integers from 1 to 10
R is a hydrogen or $C_1$- to $C_6$-alkyl
$R^2$ is an alkylene or alkylidene group having 1 to 6 carbon atoms or an arylene or alkylarylene group having from 6 to 20 carbon atoms
$R^3$, $R^4$, $R^5$, $R^6$ independently from each other are an alkylene or alkylidene group having 1 to 6 carbon atoms or an arylene or alkylarylene group having from 6 to 20 carbon atoms,
Z is a cation, and
n is an integer being two or higher.

9. A process according to claim 8, whereby allyl glycidyl ether is reacted with hydroxyethylidenediphosphonic acid or its salts.

10. A process of inhibiting scale deposition from an aqueous system, the process comprising the step of adding an oligomer or polymer according to claim 5 to the aqueous system.

11. A process according to claim 10, wherein the aqueous system is the formation water associated with an oilwell and/or the water injected into an oilwell to aid oil recovery.

12. A process according to claim 10, wherein the scale comprises the carbonates and/or sulphates of one or more of the group consisting of calcium, magnesium, barium, strontium, radium, and iron.

13. A process according to claim 10, wherein the scale inhibitor is used in an oilfield squeeze treatment.

* * * * *